United States Patent [19]

Kim et al.

[11] 4,384,044

[45] May 17, 1983

[54] PRODUCTION OF MICROBIAL POLYSACCHARIDES

[75] Inventors: Leo Kim, Alamo, Calif.; Stuart G. Ash, Sittingbourne, England

[73] Assignee: Shell Oil Company, Houston, Tex.

[21] Appl. No.: 293,920

[22] Filed: Aug. 18, 1981

[30] Foreign Application Priority Data

Aug. 19, 1980 [GB] United Kingdom ............... 8026977

[51] Int. Cl.$^3$ ..................... C12P 19/04; C12R 1/38; C12N 11/14
[52] U.S. Cl. ................................. 435/101; 435/874; 435/176; 166/246
[58] Field of Search ............................. 435/101–104, 435/174, 176

[56] References Cited

U.S. PATENT DOCUMENTS

| | | | |
|---|---|---|---|
| 4,247,645 | 1/1981 | Meijer-Hoffman et al. | 435/262 |
| 4,286,061 | 8/1981 | Messing et al. | 435/176 |
| 4,304,857 | 12/1981 | Brouillard et al. | 435/94 |
| 4,304,906 | 12/1981 | Kang et al. | 435/101 X |
| 4,332,904 | 6/1982 | Kurane et al. | 435/262 |

*Primary Examiner*—Lionel M. Shapiro

[57] ABSTRACT

This invention relates to a process for the production of a polysaccharide wherein a microorganism species which produces polysaccharide (preferably in the stationary phase of the growth cycle) is supported on a porous, particulate inert support, the pore size being greater than about 0.5 $\mu$m, to form an immobilized cell system, aqueous nutrient medium is passed through the immobilized system, and polysaccharide-containing medium is withdrawn from the system. The invention provides also for the use of the polysaccharide in the displacement of fluid from subsurface formations, and an immobilized cell system for use in the foregoing process.

9 Claims, No Drawings

PRODUCTION OF MICROBIAL POLYSACCHARIDES

BACKGROUND OF THE INVENTION

1. Field of the Invention

This invention relates to the use of microbial cells in an immobilized system, and in particular to the production of a polysaccharide from immobilized microorganisms.

2. Description of the Prior Art

The use of immobilization techniques has become well established in biochemical transformations using enzymes, and more recently this technique has been applied also to whole microbial cells. However, hitherto such immobilized cell technology has been applied primarily to the production of relatively low molecular weight organic molecules, such as aspartic acid, tryptophan and aminopenicillanic acid, and has not been applied to the production of higher molecular weight materials such as the polysaccharides elaborated by a variety of slime-forming micro-organisms. It would be expected that the molecular size and viscosity characteristics of such products would tend to impair the effectiveness of an immobilized system and indeed no success was achieved in attempts to produce an immobilized system by gel entrapment of the cells. However, it has now surprisingly been found that polysaccharides can be produced from cells immobilized on a porous, particulate support, provided that the support particles have a defined pore size.

SUMMARY OF THE INVENTION

Accordingly, the present invention provides a process for the production of a polysaccharide wherein a microorganism species which produces a polysaccharide is supported on a porous, particulate inert support, the pore size being greater than about 0.5 $\mu$m, to form an immobilized cell system in which the microorganism cells are dispersed through pores of the inert support, aqueous nutrient medium is passed through the immobilized system, and polysaccharide-containing medium is withdrawn from the system.

This process is generally applicable to varieties of microorganisms which produce polysaccharides, but is particularly effective with those microorganisms where polysaccharide production is not necessarily associated with growth and multiplication, that is microorganisms which produce polysaccharides in the stationary phase of the growth cycle. Examples of such microorganisms are certain slime-forming species of the genera Pseudomonas, Rhizobium, Alcaligenes and Agrobacterium, especially Pseudomonas spp. NCIB 11592 and 11264, *Rhizobium meliloti, Alcaligenes faecalis* var. *myxogenes, Agrobacterium radiobacter, Agrobacterium tumefaciens* and *Agrobacterium rhizogenes.* All these specific organisms elaborate a particular polysaccharide containing glucose, galactose and pyruvate in the molar proportions 7:1:1, whose characteristics and use in oil recovery processes are desirable. Additionally, such polysaccarides may contain up to 2 succinate residues and up to 2 acetate residues, the precise proportions of these molecular components varying according to the micro-organism from which the polysaccharide is produced, and also the precise conditions under which the microorganisms is cultivated. The novel strain NCIB 11592 of Pseudomonas sp. isolated from a sample of soil from France is deposited at the National Collection of Industrial Bacteria, Torry Research Station, Aberdeen.

The above-described solid support material is naturally chemically and biologically inert under the conditions of use, and suitable materials are suitably inorganic oxides, such as natural or synthetic alumina, zirconia, magnesia and mixtures thereof or equivalent porous, particulate, inert supports. The effective retention of the microbial cells on the support has been found to be dependent on the selection of the pores in the support particles, and as indicated above this should be greater than 0.5 $\mu$m. Generally, the best results are obtained when the pore size is at least about 1 $\mu$m, and the preferred pore sizes are from about 3 $\mu$m to about 30 $\mu$m. The size of the support particles is less critical than pore size for acceptable operation, and in practice is determined partically by the operational conditions under which the immobilized system will be employed, e.g. whether retained in a fixed bed or used as a slurry. In general the particle size should be less than about 1 mm, and for operation in a slurry reactor it has been found that best results are normally attained when using particles within the size range of about 100 to about 600 $\mu$m, and preferably about 150 to about 300 $\mu$m.

The location of the cells onto the support may be carried out by a variety of techniques which will disperse the cells through the pores of the inert support, but two procedures have been found to be generally suitable. In one technique the microbial cells are cultivated by established methods in a fermenter so as to yield a paste of the required cells which is mixed with the support particles. The mixture is then subjected to a vacuum and the vacuum released so that the atmospheric pressure forces the paste into the pores. The coated particles are then allowed to age for a short period (several hours), after which the surplus cells are washed away. An alternative technique is that of growth in situ, in which the particulate carrier is suspended in a suitable growth medium, which is then inoculated with the desired organism. The inoculated, support-containing growth medium is then incubated under appropriate conditions to provide for growth of the organism, and after a suitable period free cells are removed by washing to leave the cell-containing immobilized system. In a variation of this technique, fresh growth medium containing an assimilable source of carbon and nitrogen is continuously fed into the reactor during immobilization to provide suitable conditions for attachment.

The aqueous nutrient medium should provide a substrate for the production of polysaccharide by the microorganism. In the case of those microorganisms which produce polysaccharide in the stationary phase of their growth cycle, the nutrient medium is preferably one which, whilst providing the necessary substrate, does not provide conditions conducive to growth and multiplication of the microorganism. Such non-growth conditions can be maintained by the use of a medium deficient in nitrogen or by other well established means. The aqueous nutrient medium will normally contain an assimilable source of carbon together with smaller amounts of inorganic ions. The source of carbon is suitably a carbohydrate, conveniently glucose, and is preferably employed in a concentration between about 0.1 and about 10% by weight, normally about 1-2% w/v. The temperature and pH at which polysaccharide is most effectively produced will naturally vary according to the organism, and in the case of Pseudomonas sp.

NCIB 11592 the temperature is preferalby between 20° and 35° C., and the pH preferably between 6 and 9. During production of polysaccharide the aqueous nutrient medium will normally be fed continuously into the immobilized system at the same rate as the polysaccharide-containing outlet medium is withdrawn therefrom; that outlet medium can be used per se or may be treated according to conventional procedures to extract the polysaccharide therefrom.

One important use of the polysaccharides produced by this invention is in enhanced oil recovery because of their pseudo-plastic or shear-thinning properties. Hence the invention includes also a process in which the polysaccharide-containing medium, after any conventional concentration adjustment and/or incorporation of additional compounds, is injected into a fluid-bearing permeable subsurface formation and the displaced fluid from the formation is produced. In this application it is particularly important for the polysaccharide solution to be free from cell bodies, and an advantage of the process of this invention is that it simplifies the production of a cell-free polysaccharide solution. Using conventional processes it is necessary to separate the microbial cells from the viscous solution of polysaccharide, but in the process of this invention the cells are immobilized on the support and hence the resultant polysaccharide solution is substantially free from such cells.

The invention is illustrated in the following non-limiting Examples.

EXAMPLE I

Characterization of Pseudomonas sp. NCIB 11592

Pseudomonas sp. NCIB 11592 has the morphological and physiological characteristics set out below. These were determined by standard test methods described in "Cowan and Steel's Manual for the Identification of Medical Bacteria", second edition (1974). Comparison of these characteristics with those listed in "Bergy's Manual of Determinative Bacteriology, Eigth Edition" indicates that the organism has many characteristics of the genus Pseudomonas but certain properties which are normally associated with Agrobacterium, though the production of a water-soluble pigment under certain conditions suggests that Pseudomonas is the more appropriate designation.

1. Physical Characteristics

| (a) | Shape | small rods, occurring singly or in pairs. 0.5–1.0 microns, × 1.5–2.5 microns. |
| (b) | Motility | motile with 1 or 2 polar flagella |
| (c) | Sporulation | no evidence of spore (or cyst) formation. |
| (d) | Gram stain | negative. |

2. Cultural characteristics

Nutrient agar plate. Colonies off-white, smooth glistening flat, circular and entire. Diameter 2–3 mm after 24 h at 30° C.

3. Physiological characteristics

| (a) | Catalae | positive |
| (b) | Oxidase | positive |
| (c) | Urease production | positive |
| (d) | Growth | aerobic |
| | | Anaerobic with nitrate |
| (e) | Temperature relations | up to 37° C., optimum 30° C. No growth at 4° C. or 41° C. |
| (f) | pH relations | optimum 6.5–7.5, range 4.5–9.0 |
| (g) | Methyl red | negative |
| (h) | Voges-Proskauer | negative |
| (i) | Carbohydrate breakdown | oxidative |
| (j) | $H_2S$ production | negative |
| (k) | Indole production | negative |
| (l) | Nitrate reduction | positive, $N_2$ or $NH_3$ formed |
| (m) | Hydrolysis of | |
| | gelatin | negative |
| | Tween | negative |
| | Casein | negative |
| | starch | negative |
| (n) | Litmus milk | reduced |
| (o) | Arginine dihydrolase (Thornley's test) | negative |
| (p) | Arginine decarboxylase | negative |
| | Lysine decarboxylase | negative |
| | Ornithine decarboxylase | negative |
| (q) | Pigmentation | Kings B medium - slight yellow |
| (r) | Utilization of carbon sources - Grows on glucose, sucrose, fructose, succinate, serine, alanine, mannitol, lactate, and propylene glycol. Acid produced from glucose. No growth on citrate, malonate, phenylalanine, gluconate, ethanol or ethylene glycol. | |
| (s) | Bernaerts and De Ley test | positive |

A. Preparation of immobilized system

(1) Vacuum loading

Pseudomonas sp. NCIB 11592 was continuously cultivated in a Chemap LF-7 fermentation vessel having a liquid volume of 4 l. The culture temperature was maintained at 28° C. and the pH controlled at 6.8 by the automatic addition of 2 N alkali solution (1 N NaOH and 1 N KOH). Air was sparged into the fermenter at 0.5 l min$^{-1}$ and the culture was agitated by a mixture impeller revolving at 1000 rpm. Fresh sterile medium in two streams was pumped into the fermenter continuously and culture broth withdrawn by a weir to maintain a constant working volume in the reactor. The flow rates and composition of the streams were as follows:

Stream 1. Flow rate: 300 ml h$^{-1}$

Mineral salts medium as defined below containing also 20 g$^{-1}$ glucose and 10 mM $H_3PO_4$.

| | Concentration | | |
| Component | gl$^{-1}$ | mM | μM |
| --- | --- | --- | --- |
| $MgSO_4.7H_2O$ | 0.493 | 2.0 | |
| $CaCl_2.2H_2O$ | 0.147 | 1.0 | |
| $FeSO_4.7H_2O$ | 55.6 × 10$^{-3}$ | | 200 |
| $MnSO_4.7H_2O$ | 4.46 × 10$^{-3}$ | | 20 |
| $ZnSO_4.7H_2O$ | 5.74 × 10$^{-3}$ | | 20 |
| $CuSO_4.5H_2O$ | 4.99 × 10$^{-3}$ | | 20 |
| $CoCl_2.6H_2O$ | 2.37 × 10$^{-3}$ | | 10 |
| $H_3BO_3$ | 0.61 × 10$^{-3}$ | | 10 |
| $Na_2MoO_4.2H_2O$ | 2.41 × 10$^{-3}$ | | 10 |
| KI | 1.66 × 10$^{-3}$ | | 10 |

Stream 2. Flow rate: 60–120 ml h$^{-1}$ $(NH_4)_2SO_4$  21.14 gl$^{-1}$

A paste of the cells prepared from the broth by centrifugation and containing 100 g cells (dry weight) per liter was mixed with the chosen support particles. This mixture was then evacuated by water pump and the vacuum released after 3–5 minutes. This procedure was repeated to 4 to 5 times and the mixture was aged at 4° C. for 2 h or 12 hours before repeated washing with a phosphate buffer solution to remove excess cells. The cell loading attained was estimated either by respiration studies using an oxygen electrode, or by measuring the concentration of protein using the method of Lowrey et al., and was expressed as mg dry weight of cells per gram of support material. These tests were carried out with a variety of support materials. The results of all these tests are summarized in Table 1 below.

TABLE 1

| Designation | Support Material Composition | Pore Size (μm) | Particle Size (μm) | Aging Time | Cell Loading (mg. dry wt./gm support) |
|---|---|---|---|---|---|
| Fractosil 5000 | Silica | 0.5 | 63–125 | 2 | 0.1 |
| Fractosil 10000 | " | 1.0 | " | 2 | 4.4 |
| Fractosil 25000 | " | 2.5 | " | 2 | 3.3 |
| Fractosil 25000 | " | 2.5 | " | 12 | 21/26 |
| Fractosil 5000 | " | 0.5 | " | 12 | 5.33 |
| Norton 06519 | Alumina | 3–13 | 150–250 | 2 | 10.7 |
| " | " | " | 300–600 | 12 | 11.5 |
| " | " | " | >600 | 12 | 8.0 |
| Norton 06482 | Silica/Alumina | " | 150–300 | 2 | 11.2 |
| Norton SA 5221 | Alumina | 10–30 | N.A. | 12 | 10.1 |
| Norton SA 5564 | Zirconia | 5–80 | N.A. | 12 | 9.4 |
| Norton SA 6525 | Alumina | 3.2 | N.A. | 12 | 9.1 |
| Norton SA 5231 | Alumina | 1-2/15–100 | N.A. | 12 | 4.9 |
| Norton SA 6605 | Alumina | 5 | N.A. | 12 | 10.8 |
| Carborundum SAEHS4533 | " | 0.3 | N.A. | 2 | zero |
| Harshaw AL-183-1P | " | N.A. | 500 | 2 | 3.3 |

(2) Loading by growth in situ

Pseudomonas sp. NCIB 11592 was cultivated in a Biotec fermenter having a working volume of 2.5 l in the presence of 5–10% by w/v of alumina (Norton 06519) particles using a gas flow rate of 400 ml/min of air or 200 ml/min oxygen and an agitator speed of 200 rpm, giving a dissolved oxygen tension greater than 60% air saturation. The temperature was 30° C., the pH was controlled at 7.0 by the automatic addition of 2 N alkali solution, and the growth medium comprised the mineral salts medium as defined above, containing also 20 g/l glucose, 2.11 g/l NH$_4$SO$_4$, 0.680 g/l KH$_2$PO$_4$ and 0.709 g/l Na$_2$HPO$_4$.

Immediately before batch growth finished (about 20 hours), reactor conditions were changed to a gas flow rate of 600 ml/min air (or 300 ml/min oxygen) and continuous culture using the given medium at a flow rate in excess of 1 l/h. At this high dilution rate the cells already attached to the carrier were retained and grew further in the carrier, while the free, or loosely secured, cells were washed out. Cells were cultivated in this manner until no further increase in cell loading was observed (48 hours), and the cell loading determined as in A(1). The results are set out in Table 2 below.

TABLE 2

| | Loading (mg g$^{-1}$) | |
|---|---|---|
| Time from start of continuous culture (h) | RUN 1 72 gl$^{-1}$ carrier conc. | RUN 2 260 gl$^{-1}$ carrier conc. |
| 0 | 4.0 | 3.5 |
| 20 | 10.5 | 12.0 |
| 40 | 17.4 | n.d. |
| 60 | 17.2 | 20 |
| 80 | — | 20 |

B. Production of biopolymer (1) Vacumm immobilisation and batch production

Cells of Pseudomonas sp. NCIB 11592, Pseudomonas sp. NCIB 11264 and *Agrobacterium radiobacter* NCIB 9042 were immobilised onto alumina, (Norton 06519) as described previously. 10 g of each biocatalyst, after washing, were placed in shake flasks containing 100 ml of 10 mM phosphate buffer at pH 7.4 and 10 g glucose. The flasks were shaken at 200 rpm and 30° C. with the following results:

TABLE 3

| Strain | Loading[1] (mg g$^{-1}$) | Polymer concentration after 140 h (gl$^{-1}$) |
|---|---|---|
| Pseudomonas sp. NCIB 11592 | 9.6 | 4.0 |
| Pseudomonas sp. NCIB 11264 | 11.0 | 4.5 |
| *Agrobacterium radiobacter* NCIB 9042 | 8.5 | 2.0 |

Notes:
[1] mg cells (dry wt)/g support (2) Vacuum immobilisation and continuous production Cells of Pseudomonas sp. NCIB 11592 were immobilised onto alumina (Norton 06519) as described previously, to give 9.7 mg cells (dry weight)/g support. 180 g of the biocatalyst were placed in a 4 liter Biotec fermentation vessel containing 2.8 l of medium comprising the mineral salts medium described previously and also 20 g/l of glucose and 10 mM H$_3$PO$_4$. The temperature was maintained at 30° C. and the pH controlled at 7.0 by the automatic addition of 2 N alkali solution. Air was sparged into the reactor at 400 ml/min and the suspension was agitated by an impeller rotating at 200 rpm. Fresh medium was pumped into the reactor at 225 ml h$^{-1}$ and polysaccharide solution was withdrawn by a weir, incorporating a settler, to maintain a constant working volume and constant biocatalyst hold-up in the reactor. The polysaccharide concentration in the outlet stream (as measured by reaction with anthrone) is shown in the following table:

TABLE 4

| Run time (hours) | Polysaccharide Concentration (gl$^{-1}$) |
|---|---|
| 20 | 0.15 |
| 42 | 0.13 |
| 63 | 0.18 |
| 114 | 0.20 |

TABLE 4-continued

| Run time (hours) | Polysaccharide Concentration (gl$^{-1}$) |
|---|---|
| 139 | 0.21 |

(3) Immobilisation by growth in situ and continuous production

Pseudomonas sp. NCIB 11592 was immobilised onto 180 g of alumina, (Norton 06519), according to the procedures in Example A2. Following immobilisation, fresh salts medium (nitrogen free) containing also 20 g/l glucose and 10 mM $H_3PO_4$ was pumped into the reactor at 225 ml h$^{-1}$ and polysaccharide solution was withdrawn as in Example B2. After initial loss of cells, the loading of cells on the support during polymer synthesis stabilised at 10 mg (dry wt)/g. The polysaccharide concentration in the outlet stream is shown in the following table:

TABLE 5

| Run time (hours) (following immobilisation) | Polysaccharide concentration (gl$^{-1}$) |
|---|---|
| 26 | 0.73 |
| 42 | 0.51 |
| 63 | 0.45 |
| 86 | 0.45 |

(4) Growth in situ at different nutrient levels and continuous production

Pseudomonas sp. NCIB 11592 was immobilised onto alumina (Norton 06519) according to the procedures in Example A2, except that the growth medium contained the following mineral salt concentrations:

| Component | Concn. mg/l |
|---|---|
| $Na_2HPO_4$ | $3.0 \times 10^3$ |
| $KH_2PO_4$ | $3.0 \times 10^3$ |
| $MgSO_4.7H_2O$ | $0.2 \times 10^3$ |
| $FeCl_3.6H_2O$ | 33.4 |
| $CaCl_2.2H_2O$ | 16.0 |
| $ZnSO_4.7H_2O$ | 0.36 |
| $CuSO_4.5H_2O$ | 0.32 |
| $MnSO_4.4H_2O$ | 0.30 |
| $CoCl_2.6H_2O$ | 0.36 |
| $H_3BO_3$ | 0.20 |
| $Na_2MoO_4.2H_2O$ | 0.60 | together with $(NH_4)_2SO_4$ and glucose in the concentrations of either 0.3 g/l and 10 g/l (I) or 3.0 g/l and 20 g/l (II) respectively. The time of loading growth was 90 hours for I and 70 hours for II. The resulting immobilised cell systems were then supplied with nutrient medium which differed from the growth medium only in the omission of the ammonium sulphate (this modification being referred to as nitrogen-free medium), the polysaccharide solution withdrawn, and the product quotient (g.polymer/g. fixed cells/hr) and productivity (in terms of mg polysaccharide/g. cell-bearing support/hr) determined. The results are set out in Table 6 below, from which it will be apparent that the higher nutrient levels lead to significant improvements in cell loadings and the production parameters.

TABLE 6

| Time (hrs) | Cell loading (mg/g) I | II | Product Quotient I | II | Productivity I | II |
|---|---|---|---|---|---|---|
| 0 | 11.04 | 53.2 | 0.007 | 0.002 | 0.074 | 0.107 |
| 16.4 | 8.77 | — | 0.051 | — | 0.449 | — |
| 17.5 | — | 26.1 | — | 0.022 | — | 0.570 |
| 40.5 | 7.4 | — | 0.065 | — | 0.483 | — |
| 53.1 | — | 13.2 | — | 0.045 | — | 0.593 |
| 65.0 | 5.55 | — | 0.048 | — | 0.268 | — |
| 78.1 | — | 11.2 | — | 0.065 | — | 0.728 |
| 89.3 | — | 11.97 | — | 0.039 | — | 0.467 |
| 99.9 | 4.45 | — | 0.040 | — | 0.178 | — |
| 113.2 | — | 9.64 | — | 0.034 | — | 0.330 |
| 126.5 | 4.13 | — | 0.021 | — | 0.086 | — |
| 136.5 | 4.11 | — | 0.028 | — | 0.113 | — |
| 137.3 | — | 10.59 | — | 0.034 | — | 0.360 |
| 161.0 | 3.98 | — | 0.015 | — | 0.059 | — |
| 161.6 | — | 8.6 | — | 0.029 | — | 0.251 |
| 183.9 | 5.64 | — | 0.012 | — | 0.065 | — |
| 185.4 | — | 8.96 | — | 0.034 | — | 0.301 |
| 242.2 | 3.12 | — | 0.030 | — | 0.092 | — |
| 246.3 | — | 9.4 | — | 0.019 | — | 0.174 |

Example II

Regeneration of polysaccharide productivity

Pseudomonas sp. NCIB 11592 was immobilised onto alumina (Norton 06519) following the procedure of Example B4, with the higher nutrient levels and a loading time of 76 hours. This immobilised cell system was then supplied at a dilution rate of 0.08 hr$^{-1}$ (being the flow of medium divided by the volume of liquid in the reactor) with nitrogen-free (but otherwise similar) medium to initiate a polysaccharide production phase, which was operated for 208 hours. By this time the polysaccharide product quotient had dropped to a low level, and the nitrogen-free medium was replaced by the complete, nitrogen-containing growth medium at a dilution rate of 0.4 hr$^{-1}$ for a period of 96 hours in order to regenerate the polysaccharide producing cell activity. After that regenerative phase, the production phase was resumed by reintroducing the nitrogen-free medium at a dilution rate of 0.08 hr$^{-1}$. The cell loadings and polysaccharide product quotient were determined throughout this experiment and are set out below in Table 7, from which it will be apparent that the regeneration procedure effectively restores the polysaccharide productivity of the immobilised system.

TABLE 7

| Time (hrs) | Cell Loading (mg/g) | Product Quotient |
|---|---|---|
| 0 | 35.0 | 0.001 |
| 16.25 | 20.4 | 0.010 |
| 39.43 | 14.0 | 0.034 |
| 74.34 | 9.17 | 0.030 |
| 96.2 | 9.19 | 0.016 |
| 111 | 8.6 | 0.02 |
| 135 | 8.9 | 0.011 |
| 159 | 6.98 | 0.007 |
| 183 | 6.8 | 0.005 |
| 208 | 6.8 | 0.010 |
| 240 | 21.7 | |
| 262 | 38.2 | Regeneration Phase |
| 281 | 36.9 | |
| 302 | 35.7 | |
| 331/0 | 35.0 | 0.007 |
| 16.7 | 22.1 | 0.021 |
| 41.8 | 16.97 | 0.046 |
| 77.4 | 14.5 | 0.063 |
| 100.8 | 15.3 | 0.043 |
| 114.8 | 12.64 | 0.049 |

TABLE 7-continued

| Time (hrs) | Cell Loading (mg/g) | Product Quotient |
|---|---|---|
| 142 | 13.9 | 0.039 |

EXAMPLE III

To demonstrate the results obtained from an organism which required growth to produce polymer, a paste of *Xanthomonas campestris* ATCC 13951 was loaded by growth in situ onto three different supports. Each system (10 g) was then placed into 100 ml of a 100 mM tris buffer at pH 7.4 containing 1% glucose and the polymer production determined using procedures similar to those of B(1) above. The results are shown in the table below.

TABLE 8

| Support Material | Cell Loading (mg/g) | Polymer concentration after 140 hr (gl$^{-1}$) |
|---|---|---|
| Norton alumina, batch 06519 | 6.8 | 1.4 |
| Norton silica/alumina, batch 06482 | 7.2 | 0.3 |
| Fractosil 25000 (Merck, Darmstadt) | 8.8 | 0.7 |

It will be seen that polymer is generated, although the rate is lower than that achieved with Pseudomonas sp. NCIB 11592.

COMPARATIVE EXAMPLE

Alternative immobilisation techiques

The following Examples show that the immobilisation techniques of this invention are necessary for efficient polysaccharide production, since alternative conventional techniques are unsuitable.

(1) Immobilisation by covalent attachment

Suitable supports were activated by the following coupling reagents: 1-ethyl-3-(3'-dimethylaminopropyl) carbodiimide, glutaraldehyde, quinone and N-hydroxy succinimide. Activated supports were mixed with a cell paste of Pseudomonas sp. NCIB 11592 for several hours to effect immobilisation. In all cases there was either no significant binding of cells or the cells that did bind lost activity for polysaccharide synthesis.

(2) Immobilisation by gel entrapment

Techniques for the immobilisation of cells in gels are well documented in the literature. Cells of Pseudomonas sp. NCIB 11592 were immobilised by entrapment in the following gels: agar, polyacrylamide, calcium alginate. In all cases the cells were successfully immobilised and retained the ability to respire in the presence of glucose solution. However, no polymer was released into solution. It is expected that the pores in the gels are too small to allow the export of the polymer from the particles.

We claim:

1. A process for the production of a polysaccharide wherein a microorganism species selected from Pseudomonas spp. NCIB 11592 or NCIB 11264 is supported on a porous, particulate-insert support, the pore size being greater than about 0.5 μm, to form an immobilized cell system in which the microorganism cells are dispersed through the pores of the inert support system, aqueous nutrients medium is passed through the immobilized cell system, and polysacchardide-containing medium is withdrawn from the system.

2. A process according to claim 1, wherein the microorganism is a species which produces the polysaccharide in the stationary phase of the growth cycle.

3. A process according to claim 1 wherein the support is an inorganic oxide.

4. A process according to claim 1 wherein the pore size is from about 3 to about 30 μm.

5. A process according to claim 1 wherein the particles of the inert support have a mean diameter of less than about 1 mm.

6. A process according to claim 5 wherein the mean particle diameter is from about 100 to about 600 mm.

7. A process according to claim 1 wherein the location of the microorganisms on the support is effected by mixing the support with a paste of the microorganism, subjecting the mixture to a reduced pressure, and subsequently restoring atmospheric pressure.

8. A process according to claim 1 wherein the location of the microorganisms on the support is effected by growing the microorganisms in the presence of the support.

9. A process according to claim 1 wherein the polysaccharide-containing medium, after any necessary concentration adjustment and/or incorporation of additional compounds, is injected into a fluid-bearing permeable subsurface formation and the displaced fluid form the formation is produced.

* * * * *